United States Patent [19]
Oettel et al.

[11] Patent Number: 5,633,242
[45] Date of Patent: May 27, 1997

[54] PHARMACEUTICALS FOR CONTRACEPTION/HORMONE SUBSTITUTION CONTAINING A BIOGENOUS ESTROGEN COMPONENT

[76] Inventors: Michael Oettel, Beethovenstrasse 30, 07743 Jena; Hermann Osterwald, Rasenweg 14, 37120 Bovenden; Claudia Moore, Novalisstrasse 23, 07747 Jena; Thomas Gräser, Heinrich-Hertz-Strasse 7, 99097 Erfurt, all of Germany

[21] Appl. No.: 511,026

[22] Filed: Aug. 3, 1995

[30] Foreign Application Priority Data

Aug. 12, 1994 [DE] Germany .................. 44 29 374.7

[51] Int. Cl.$^6$ ............................................. A61K 31/56
[52] U.S. Cl. .................. 514/170; 514/841; 514/843
[58] Field of Search ........................ 514/170, 841, 514/843

[56] References Cited

U.S. PATENT DOCUMENTS

| | | | |
|---|---|---|---|
| 3,639,600 | 2/1972 | Hendrix | 424/242 |
| 4,921,843 | 5/1990 | Pasquale | 514/170 |
| 5,010,070 | 4/1991 | Boissonneault | 514/171 |

FOREIGN PATENT DOCUMENTS

| | | |
|---|---|---|
| 3213248 | 11/1982 | Germany . |
| 2645307 | 10/1988 | Germany . |
| 3229612 | 7/1992 | Germany . |
| 4104385 | 8/1992 | Germany . |
| 4224534 | 1/1994 | Germany . |
| 4308406 | 6/1994 | Germany . |

OTHER PUBLICATIONS

Zhu et al., "The Carcinogenic Activity of Ethinyl Estrogen Is Determined by Both Their Hormonal Characteristics and Their Conversion to Catechol Metabolites", Endocrinology, vol. 132, No. 2, pp. 577–583 (1993).

Jiang et al., "Effect of 17β–oestradiol on contraction, $Ca^{2+}$ current and intracellular free $Ca^{2+}$ in guinea–pig isolated cardiac myocytes", Pharmacol (1992), 106, pp. 739–745.

Mooradian, "Antioxidant Properties of Steroids", J. Steroid Biochem, Molec. Biol., vol. 45, No. 6, pp. 509–511, 1993.

Jiang et al., "Acute effect of 17β–estradiol on rabbit coronary artery contractile responses to endothelin–1", Am. J. Physiol., 263 pp. H271–275, 1992.

Clarkson, "Experimental effects of progesterone versus progestins on arterial wall", Gynecol. Endocrinal., 6 Suppl. 1:15, 1992.

Primary Examiner—Kimberly Jordan
Attorney, Agent, or Firm—Webb Ziesenheim Bruening Logsdon Orkin & Hanson, P.C.

[57] ABSTRACT

This invention relates to a compound preparation for contraception and hormone replacement that consists of three steps totalling 28 daily doses. The pharmaceutical is characterized in that step 1 consists of 3 or 4 daily doses, each containing a preparation in which the active ingredient is at least one biogenous estrogen component, step 2 consists of 20 to 22 daily doses, each containing a preparation in which the active ingredients are at least one biogenous estrogen and one gestagen component from the group of $C_{21}$-gestagens including progesterone, as well as dienogest, desogestrel, 3-keto desogestrel, gestodene, levonorgestrel, norgestimate, norethisterone, norethisterone acetate and dydrogesterone, and step 3 consists of 3 or 4 daily doses, each containing a preparation in which the active ingredient is at least one biogenous estrogen component.

6 Claims, No Drawings

1

PHARMACEUTICALS FOR CONTRACEPTION/HORMONE SUBSTITUTION CONTAINING A BIOGENOUS ESTROGEN COMPONENT

FIELD OF THE INVENTION

This invention relates to contraceptives with a natural estrogen component and high cycle stability that can be used for hormone replacement both during menopause and postmenopause, and which are preferably applied in a 28-day cycle.

BACKGROUND OF THE INVENTION

Oral contraceptives are the most frequently used form of medicamentous birth control today and very likely in the future as well. Such contraceptives were first introduced to the market in the early 1960s and have been continually improved through intensive research. In particular, the required dosage of the active ingredient was reduced so that today's oral contraceptives are dosed much lower. Besides less preferred pharmaceuticals with just a gestagen component as their active ingredient(mini-pills), oral contraceptives consist, as a rule, of an estrogen and a gestagen component. Hormones are given in the most various combinations and doses in the form of step or phase medicines that are taken over a period of 21 days followed by a 6-day interruption.

Such pharmaceuticals are known, for example, from the German patents DE-PS 32 29 612, DE-PS 41 04 385, U.S. Pat. No. 4,921,843, and German patent DE-PS 43 08 406.

The steroids that are used as gestagen component may be quite different in their chemical structure. Typical gestagens are steroids with a 17β-ethinyl group and a 13-ethyl group such as desogestrel and 3-keto desogestrel, gestodene, levonorgestrel and norgestimate, as well as norethisterone, a 13-ethyl compound, or norethisterone acetate, and gestagens without a 17β-ethinyl group but with a 13-methyl group such as progesterone, chlormadinone acetate, cyproterone acetate, medroxyprogesterone acetate, megestrol acetate, dydrogesterone, dienogest, etc. The various gestagens are mainly responsible for ovulation inhibition and proper transformation of the endometrium. When these sex hormones are no longer applied, the so-called (menstruation-like) withdrawal bleeding occurs.

The estrogen component is mainly responsible for the correct development (proliferation) of the endometrium (uterine mucosa) according to the cycle and thus for sufficient cycle control. Preferred estrogen components are the synthetic estrogen ethinyl estradiol that has been known for 40 years or mestranol, its 3-methyl ester. The latter is a prodrug that, after resorption and passage through the liver, is transformed into ethinyl estradiol, its active form. Other synthetic estrogens such as stilbene and moxestrol have not proved to be useful due to the high toxic risk they pose.

Synthetic introduction of the 17β-ethinyl group prevents conversion of 17β-estradiol, the parent substance, to the much less effective estrone, which guarantees a good proliferative effect on the endometrium and good cycle stability even at extremely low doses of 0.02 to 0.03 mg a day. Ethinyl estradiol or its prodrug mestranol, however, have a number of serious toxicological and pharmacological disadvantages. Thus ethinyl estradiol is resorbed badly and quite differently from person to person in the gastrointestinal tract which results in insufficient bioavailability. Furthermore, application of ethinyl estradiol significantly increases the risk of thrombosis or thromboembolism. Ethinyl estradiol also acts as a suicidal inhibitor on certain isoenzymes of the cytochrome P-450 system. This leads to an inhibition of endogenous catabolic and metabolic pathways. As gestagens and many other active ingredients are decomposed and metabolized to a major extent via these pathways as well, repeated application causes accumulation of these agents in the body. Other undesired side effects are a rise in blood pressure due to the induction of angiotensinogen or renin in the liver, and the carcinogenic capability of this substance (Bao Thing Zhu, Roy D. Liehr J: The carcinogenic activity of ethinyl estrogens is determined both by their hormonal characteristics and their conversion to catechol metabolites. Endocrinology 132:577–583, 1993).

Despite these considerable disadvantages, no alternative agents for use as oral contraceptives were found. There is still a great need for toxicologically less unsafe compounds for use as contraceptives.

One toxicologically safer compound that could be used is endogenous 17β-estradiol that could be administered in micronized form or as a fatty acid ester (e.g. estradiol valerate). This non-synthetic hormone holds a number of pharmacological and toxicological advantages, for example, its hypotensive effect (Clarkson, T B: Experimental effects of estradiol versus progestins on arterial wall. Gynecol. Endocrinol. 6, Suppl. 1, 15; 1992), reversal of contraction of the vessels caused by endothelins (Jiang C, Poole-Wilson P A, Sarrel P M, Campbell S, Collins W: Effect of 17β-estradiol on contraction, $Ca^{2+}$ current and intracellular free $Ca^{2+}$ in guinea pig isolated cardiac myocytes. Br. J. Pharmacol. 104: 739, 1992; Jiang C, Sarrel P M, Poole-Wilson P A, Collins W: Acute effect of 17β-estradiol on rabbit coronary artery contractile responses to endothelin-1. Am. J. Physiol. 263: H271, 1992), inhibition of lipid peroxidation in cell membranes and of LDL cholesterol oxidation as initial steps of an atherosclerosis (Mooradian A D: Antioxidant properties of steroids. J. Steroid Biochem. 45: 509–511, 1993), deceleration of osteoclasts and thus of osteoclasis as part of an osteoporosis prevention or treatment, and alleviation of Alzheimer-type senile dementia.

These advantages of 17β-estradiol have resulted in its frequent use in hormone replacement therapy (HRT) during menopause and postmenopause in women as described, for example, in German patents DE-PS 32 13 248 and DE-PS 26 45 307.

Use of this endogenous hormone together with a gestagen component as the only estrogen component of compound preparations for contraception was prevented by the occurrence of unacceptable disorders of the menstrual cycle; there was no breakthrough despite much effort on the part of researchers. The gestagen component of such compound preparations gives good and safe contraceptive protection but there is frequent intermenstrual bleeding as gestagen stimulates local enzymes that cause increased inactivation of the estradiol contained in the endometrium which sharply reduces the effect of estradiol on the endometrium. What has been described so far are compound contraceptives that contain both synthetic and biogenous estrogens. The resulting advantage is that much lower active ingredient concentrations are required (DE-PS 43 08 406). Still, use of synthetic estrogens has not yet been completely dispensed with.

As endogenous estrogens could not be used for contraception to any satisfactory extent, an acceptable "pill" for women to be used at all stages of life, i.e. for contraception in their fertile period and, at the same time, for hormone replacement after biosynthesis of estradiol in their ovaries has ceased, that is, during menopause and postmenopause, has not been developed.

Another disadvantage of known compound or sequential preparations used for contraception is the relatively long break between the 21- to 27-day intake periods during which there is a withdrawal bleeding that simulates natural menstrual bleeding (see, for example, DE-PS 32 29 612). For example, an ovulation-inhibiting pharmaceutical is known from U.S. Pat. No. 4,921,843 that is administered as follows: after having taken the last daily doses of the second hormonal component there is a break of at least one day, preferably two days, that could be bridged by a placebo before a new daily hormone dose of the first hormonal component of the next cycle is taken. This corresponds with the opinion that prevails among experts that such an intake break of at least one day, or a significant reduction of the effective estrogen level, is a condition for triggering the withdrawal bleeding. But if estrogen is not taken, even for only one day, there may be changes in blood flow that give rise to headache (e.g. migrainous attacks). In addition, there may be short-term alterations of other metabolic parameters, for example, of hemostasis. The compound preparation described in DE-PS 41 04 385 is meant for uninterrupted administration of the estrogen component over the whole menstrual cycle but the pharmaceutical proposed there fails to overcome the difficulties that occur when biogenous estrogens are used. So there are still risks in connection with the use of endogenous estrogens in compound preparations designed for contraception.

The problem to be solved by the present invention is to develop further an ovulation-inhibiting agent of the identified kind so that it combines high contraceptive safety with perfect cycle control while positively preventing intermenstrual bleeding and side effects.

Another problem of the invention is to provide such an agent that permits the use of endogenous estrogens.

It is yet another problem of the invention to provide an agent that can be used in women both for contraception and for hormone replacement during menopause and postmenopause.

SUMMARY OF THE INVENTION

These problems are solved according to the invention by providing a three-step compound preparation for contraception and hormone replacement that is given in 28 daily doses and comprises a step 1 that consists of 3 or 4 daily doses, each containing a preparation in which the active ingredient is at least one biogenous estrogen component, a step 2 that consists of 20 to 22 daily doses, each containing a preparation in which the active ingredients are at least one biogenous estrogen and one gestagen component from the group of $C_{21}$-gestagens including progesterone, as well as dienogest, desogestrel, 3-keto desogestrel, gestodene, levonorgestrel, norgestimate, norethisterone, norethisterone acetate and dydrogesterone, and a step 3 that consists of 3 or 4 daily doses, each containing a preparation in which the active ingredient is at least one biogenous estrogen component.

DETAILED DESCRIPTION OF THE INVENTION

The present invention relates to a compound preparation for contraception and hormone replacement that consists of three steps totalling 28 daily doses. This pharmaceutical is characterized in that step 1 consists of 3 or 4 daily doses, each containing a preparation in which the active ingredient is at least one biogenous estrogen component, step 2 consists of 20 to 22 daily doses, each containing a preparation in which the active ingredients are at least one biogenous estrogen and one gestagen component from the group of $C_{21}$-gestagens including progesterone, as well as dienogest, desogestrel, 3-keto desogestrel, gestodene, levonorgestrel, norgestimate, norethisterone, norethisterone acetate and dydrogesterone, and step 3 consists of 3 or 4 daily doses, each containing a preparation in which the active ingredient is at least one biogenous estrogen component.

It is scheduled for a preferred embodiment of the invention that 17β-estradiol or its ester with a physiologically acceptable acid, or a 17β-estradiol derivative that releases 17β-estradiol in physiological conditions, or a mixture of said compounds is used as biogenous estrogen component. In accordance with the invention, the estrogen is applied over the whole cycle. As explained above, this ensures better control of the ovarian follicles and avoids possible undesired side effects that could occur if intake were interrupted for a short period of time.

The invention is based on the idea that proper selection of the gestagen component allows the development of a compound preparation for contraception in which biogenous estrogen components can be used and which at the same time provides relatively high contraceptive safety, perfect cycle stability, and efficient avoidance of intermenstrual bleeding. It was known that, as mentioned above, metabolic conversion of estradiol into the less efficient estrone that takes place in the endometrial cells is responsible for the relatively unsafe effect of the endogenous estrogen 17β-estradiol or its esters on the endometrium (and the associated untolerable cyclic disorders in younger women). 17β-dehydrogenase, the enzyme that causes this conversion, is additionally induced by the gestagens applied together with the estrogen when taking compound preparations. It was found, however, that gestagens differ significantly as regards this effect. By identifying those gestagens that cause a relatively low induction of 17β-dehydrogenase it is therefore possible to develop compound preparations that contain a biogenous estrogen component and are suited for safe contraception.

In a preferred embodiment of the compound preparations according to the invention a gestagen is used as gestagen component that causes a relatively low induction of 17β-dehydrogenase. The so-called $C_{21}$ gestagens and progesterone proved to be particularly suitable. Use of chlormadinone acetate or dienogest as gestagen component of the compound preparations of the invention is particularly preferred.

It was found, furthermore, that disorders of the menstrual cycle after oral contraception mainly occur in the second half of the cycle and that such disorders can be avoided by an additional daily dose of biogenous estrogens, for example, estradiol valerate, in this period.

Another preferred embodiment of the invention is characterized by two groups of daily doses in step 2, where group (a) comprises 7 to 9 daily doses and group (b) comprises 12 to 14 daily doses, with daily doses in both groups containing equal quantities of at least one gestagen component and daily doses of the second group containing a greater quantity of the biogenous estrogen component than the first group.

Additional estrogen is preferably given on cycle days 12 to 25. The quantity of estrogen applied additionally may, for example, be in the range from 1 to 2 mg. Where other biogenous estrogens are used, similar quantities are applied to obtain the desired effect.

As biogenous estrogens are used, the compound preparation of the invention has the additional advantage that it is suited for contraception as well as for hormone replacement during menopause and postmenopause and is therefore an acceptable "pill" for women at all stages of their lives.

An effective compound preparation according to the invention may contain, for example, the following active ingredients per daily dose:

Step 1: 2.0 mg estradiol valerate
Step 2: (a) 2.0 mg estradiol 2.0 mg dienogest
(b) 4.0 mg estradiol
2.0 mg dienogest
Step 3: 2.0 mg estradiol valerate The first step is applied in the first 4 days of a menstrual cycle, the first group (a) of the second step is applied over a period of 7 days, the second group (b) of the second step over a period of 14 days, and the third step is applied over a period of 3 days.

The combinations of active ingredients according to the invention are preferably applied in the form of galenic formulations for oral administration. These formulations may be tablets, lozenges, pills or capsules. They are manufactured in the common way using common adjuvants and substrates as described, for example, in Remington's Pharmaceutical Sciences Handbook, Hack Pub. Co., N.Y., U.S.A."

An alternative way of applying the combination of active ingredients according to the invention are vaginal suppositories and vaginal capsules. These vaginal suppositories and vaginal capsules are manufactured in the common way using the adjuvants common in galenics.

The combinations of active ingredients according to the invention may also be applied in the form of transdermal therapeutical systems (TTS) for which purpose they are introduced into a TTS in a generally known way. The operating principle of TTS may, for example, be ionophoresis or diffusion, or a combination of the two. The TTS is attached to the body at an appropriate place. The active ingredients are applied transcutaneously; the rate of application is controlled by the size of the TTS and by the voltage that may optionally be applied.

For the preferred oral application, the combinations of active ingredients for contraception and hormone replacement according to the invention are combined into a pharmaceutical package that contains the formulation which makes up the daily dosage in consecutive order. Another object of this invention are therefore such pharmaceutical packages, characterized in that they contain units of dosage in a balanced, fixed order, said order being in accordance with the steps of daily application. This pharmaceutical package may, for example, be produced in the form of a swaged package. Variations regarding daily dosages, design of the forms of application, package design, etc. are known to the expert in the field.

This patent application uses the following definitions:

"Menstrual cycle" or "cycle" refers to the known and recurring menstrual sequence of normally 28 days in women at fertile age before menopause.

"Day one" of such cycle is the first day of menstruation; the subsequent days are counted until menstruation starts again; the usual number of days is 28 but may be slightly lower or higher.

"Menopause" is the date of the last menstrual bleeding in the life of an individual woman which is retrospectively determined after menstrual bleeding has ceased for one year.

There is no growth, maturing and rupture of follicles in the ovaries any more. Endogenous estradiol production drops sharply. "Postmenopause" designates the phase that follows after menopause.

The term "estrogen" covers all hormones and compounds that have estrogenic activity, i.e. are capable of causing a physiological response similar to that triggered by endogenous estrogens in adult females, e.g. inhibition of FSH secretion.

"Estradiol" covers 17β-estradiol and all esters of endogenous estrogen according to the existing definition.

"Gestagen" refers to each compound that shows a progestagenic effect similar to that of progesterone. Typical gestagens are steroids with a 17β-ethinyl group and a 13-ethyl group such as desogestrel and 3-keto desogestrel, gestodene, levonorgestrel and norgestimate, as well as norethisterone, a 13-ethyl compound, or norethisterone acetate, and gestagens without a 17β-ethinyl group but with a 13-methyl group such as progesterone, chlormadinone acetate, cyproterone acetate, medroxyprogesterone acetate, megestrol acetate, dydrogesterone, dienogest, etc.

The following examples illustrate the present invention:

EXAMPLE 1

(Composition of one tablet for each step)

Step 1 (4 tablets)

| | |
|---|---|
| 2.0 mg | estradiol valerate, micronized to an average particle size of 3 μm |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 2 (a) (7 tablets)

| | |
|---|---|
| 2.0 mg | estradiol, micronized to an average particle size of 3 μm |
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture | and, subsequently, (b) (14 tablets)

| | |
|---|---|
| 4.0 mg | estradiol, micronized to an average particle size of 3 μm |
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 3 (3 tablets)

| 2.0 mg | estradiol valerate, micronized to an average particle size of 3 μm |
|---|---|
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

EXAMPLE 2

(Composition of one tablet for each step)

Step 1 (4 tablets)

| 2.0 mg | estradiol valerate, micronized to an average particle size of 3 μm |
|---|---|
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 2 (a) (7 tablets)

| 2.0 mg | estradiol, micronized to an average particle size of 3 μm |
|---|---|
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture | and, subsequently, (b) (14 tablets)

| 3.0 mg | estradiol, micronized to an average particle size of 3 μm |
|---|---|
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 3 (3 tablets)

| 2.0 mg | estradiol valerate, micronized to an average particle size of 3 μm |
|---|---|
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

EXAMPLE 3

(Composition of one tablet for each step)

Step 1 (4 tablets)

| 1.5 mg | estradiol valerate, micronized to an average particle size of 3 μm |
|---|---|
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 2 (a) (7 tablets)

| 1.5 mg | estradiol, micronized to an average particle size of 3 μm |
|---|---|
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture | and, subsequently, (b) (14 tablets)

| 2.5 mg | estradiol, micronized to an average particle size of 3 μm |
|---|---|
| 2.0 mg | dienogest, micronized |
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

Step 3 (3 tablets)

| 1.5 mg | estradiol valerate, micronized to an average particle size of 3 μm |
|---|---|
| 33.4 mg | lactose |
| 17.2 mg | maize starch |
| 2.1 mg | polyvinyl pyrrolidone |
| 0.3 mg | magnesium stearate |
| 57.0 mg | total weight, increased to about 75 mg by adding a common sugar mixture |

EXAMPLE 4

Similar tablet composition like in Examples 1 to 3, but chlormadinon acetate is used instead of dienogest at the same dosage.

EXAMPLE 4a

Similar tablet composition like in Examples 1 to 3, but desogestrel at a dosage of 0.150 mg is used instead of dienogest.

EXAMPLE 4b

Similar tablet composition like in Examples 1 to 3, but levonorgestrel at a dosage of 0.100 mg is used instead of dienogest.

EXAMPLE 4c

Similar tablet composition like in Examples 1 to 3, but gestodene at a dosage of 0.075 mg is used instead of dienogest.

EXAMPLE 4d

Similar tablet composition like in Examples 1 to 3, but norgestimate at a dosage of 0.100 mg is used instead of dienogest.

EXAMPLE 5

Similar tablet composition like in Examples 1 to 3, but progesterone is used instead of dienogest, its dosage at step 2 being first 200 mg, then raised to 400 mg.

EXAMPLE 6

Similar tablet composition like in Examples 1 to 3, but progesterone is used instead of dienogest, its dosage at step 2 being first 300 mg, then raised to 400 mg.

EXAMPLE 7

Tablet composition is as described in Examples 1 to 6, where the first step consists of 3 tablets, the second step consists of 7 tablets for (a) and 14 tablets for (b), and the third step consists of 4 tablets.

EXAMPLE 8

Tablet composition is as described in Examples 1 to 6, where the first step consists of 4 tablets, the second step consists of 7 tablets for (a) and 14 tablets for (b), and the third step consists of 3 tablets.

EXAMPLE 9

Tablet composition is as described in Examples 1 to 6, where the first step consists of 4 tablets, the second step consists of 9 tablets for (a) and 12 tablets for (b), and the third step consists of 3 tablets.

EXAMPLE 10

Tablet composition is as described in Examples 1 to 6, where the first step consists of 3 tablets, the second step consists of 9 tablets for (a) and 12 tablets for (b), and the third step consists of 4 tablets.

EXAMPLE 11

Tablet composition is as described in Examples 1 to 6, where the first step consists of 4 tablets, the second step consists of 8 tablets for (a) and 13 tablets for (b), and the third step consists of 3 tablets.

EXAMPLE 12

Tablet composition is as described in Examples 1 to 6, where the first step consists of 3 tablets, the second step consists of 8 tablets for (a) and 13 tablets for (b), and the third step consists of 4 tablets.

We claim:

1. A method of contraception or hormone replacement beginning on the first day of menses consisting of the steps of:

(1) administering 3 or 4 daily doses of a preparation in which the active ingredient comprises at least one biogenous estrogen component;

(2) administering 20 to 22 daily doses of a preparation in which the active ingredients comprise at least one biogenous estrogen and one gestagen component; and (3) administering 3 or 4 daily doses of a preparation in which the active ingredient comprises at lease one biogenous estrogen component, wherein the total daily doses of steps (1), (2) and (3) is 28.

2. The method of claim 1, wherein the second step consists of two groups of daily doses, the first group (a) comprising 7 to 9 daily doses and the second group (b) comprising 12 to 14 daily doses, with daily doses in both groups containing equal quantities of at least one gestagen component and the daily doses of the second group containing a greater quantity of the biogenous estrogen component than the first group.

3. The method of claim 1, wherein the biogenous estrogen component is selected from the group consisting of 17β-estradiol, an ester of 17β-estradiol with a physiologically acceptable acid, a 17β-estradiol derivative that releases 17β-estradiol in physiological conditions, and a mixture thereof.

4. The method of claim 1, wherein the gestagen component is selected from the group consisting of a $C_{21}$-gestagen, progesterone, and a mixture of a $C_{21}$-gestagen and progesterone.

5. The method of claim 1, wherein the gestagen component is selected from the group consisting of chlormadinon acetate, dienogest, and a mixture of chlormadinon acetate and dienogest.

6. The method of claim 1 wherein the gestagen component is selected from the group consisting of desogestrel, 3-keto desogestrel, gestodene, levonorgestrel, norgestimate, norethisterone, norethisterone acetate, dydrogesterone and combinations thereof.

* * * * *

UNITED STATES PATENT AND TRADEMARK OFFICE
CERTIFICATE OF CORRECTION

PATENT NO. : 5,633,242
DATED : May 27, 1997
INVENTOR(S) : Michael Oettel, Hermann Osterwald, Claudia Moore, Thomas Gräser It is certified that error appears in the above-indentified patent and that said Letters Patent is hereby corrected as shown below:

Title Page, [57] ABSTRACT, Line 1 delete "This" and insert --The--.

Column 5 Line 49 "are" should read --is--.

Claim 1 Column 10 Line 28 "lease" should read --least--.

Signed and Sealed this

Second Day of September, 1997

Attest:

BRUCE LEHMAN

Attesting Officer

Commissioner of Patents and Trademarks